United States Patent
Grim et al.

(10) Patent No.: US 7,465,283 B2
(45) Date of Patent: Dec. 16, 2008

(54) CAST ASSEMBLY WITH BREATHABLE DOUBLE KNIT TYPE PADDING

(75) Inventors: Tracy E. Grim, Thousand Oaks, CA (US); Joseph M. Iglesias, Thousand Oaks, CA (US); Wendy Henderson, Ventura, CA (US); Kelly M. Long, Woodland Hills, CA (US); Michael Campos, Sylmar, CA (US); Walter Doubleday, Jupiter, FL (US)

(73) Assignee: Ossur, hf, Reykjavik (IS)

( * ) Notice: Subject to any disclaimer, the term of this patent is extended or adjusted under 35 U.S.C. 154(b) by 370 days.

(21) Appl. No.: 11/035,134

(22) Filed: Jan. 12, 2005

(65) Prior Publication Data

US 2006/0155226 A1    Jul. 13, 2006

(51) Int. Cl.
 *A61F 5/00* (2006.01)
 *A61F 13/00* (2006.01)
 *A61F 13/06* (2006.01)

(52) U.S. Cl. .................. 602/8; 602/5; 602/6; 602/60; 602/61; 602/62; 602/63; 602/64

(58) Field of Classification Search .......... 602/6–8, 602/41–66, 1, 3
See application file for complete search history.

(56) References Cited

U.S. PATENT DOCUMENTS

| | | | |
|---|---|---|---|
| 4,479,993 A * | 10/1984 | James | 428/193 |
| 5,334,442 A | 8/1994 | Okamoto et al. | |
| 5,589,245 A * | 12/1996 | Roell | 428/85 |
| 5,651,847 A * | 7/1997 | Loeffler | 66/19 |
| 5,807,295 A * | 9/1998 | Hutcheon et al. | 602/42 |
| 6,007,505 A * | 12/1999 | Grim et al. | 602/6 |
| 6,139,513 A * | 10/2000 | Grim et al. | 602/6 |
| 6,186,966 B1 * | 2/2001 | Grim et al. | 602/6 |
| 6,268,544 B1 * | 7/2001 | Court et al. | 602/41 |
| 6,461,317 B1 * | 10/2002 | Grim et al. | 602/8 |
| 6,482,167 B2 * | 11/2002 | Grim et al. | 602/8 |
| 6,824,522 B2 * | 11/2004 | Henderson et al. | 602/6 |
| 6,929,613 B2 * | 8/2005 | Henderson et al. | 602/5 |
| 7,004,917 B2 * | 2/2006 | Henderson et al. | 602/5 |
| 2002/0035343 A1 * | 3/2002 | Darcey | 602/8 |
| 2002/0161318 A1 * | 10/2002 | Pounder et al. | 602/6 |

FOREIGN PATENT DOCUMENTS

WO    WO2006/015599    2/2006

* cited by examiner

*Primary Examiner*—Patricia M Bianco
*Assistant Examiner*—Brandon Jackson
(74) *Attorney, Agent, or Firm*—Bacon & Thomas LLC

(57) ABSTRACT

A cast or support assembly includes inner double knit padding material in which the outer layer is woven or knit to have substantial size openings, while the inner layer of the double knit material to be located against the skin of the patient is more closely woven or knit. Additional casting fabric is also provided, with this casting fabric being impregnated with water hardenable material. The outer casting fabric may include openings extending through it, so that the entire cast assembly has ventilation openings allowing air circulation to accomplish rapid drying following wetting of the assembly by sweat, rain, or by swimming, for example.

20 Claims, 6 Drawing Sheets

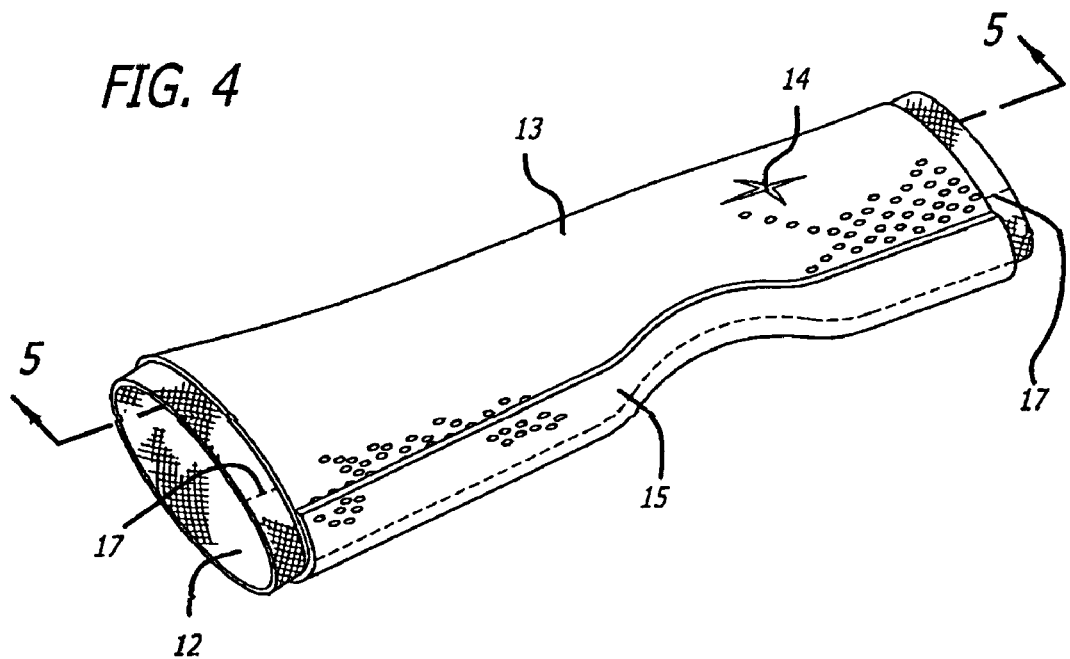
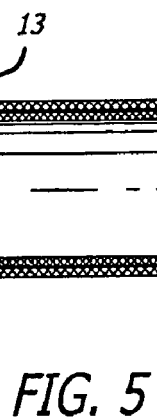

FIG. 11
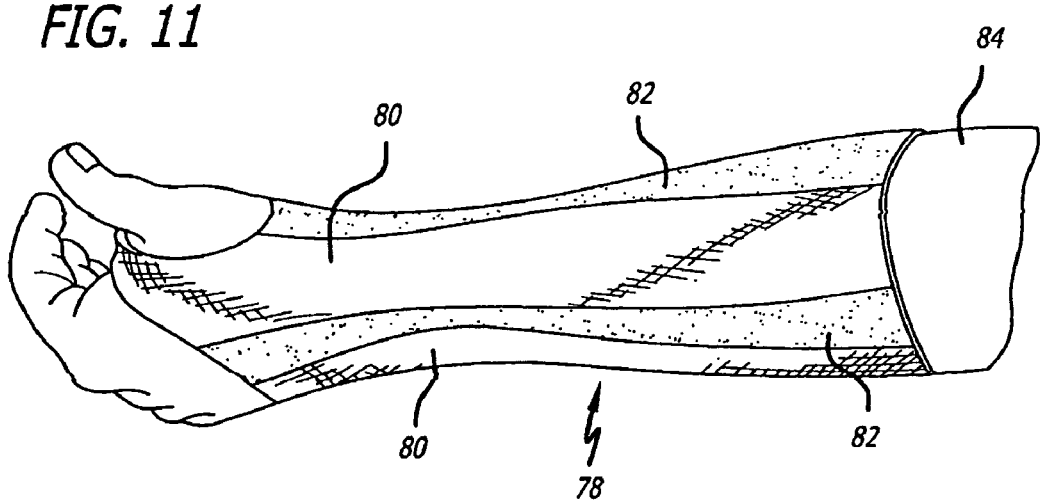
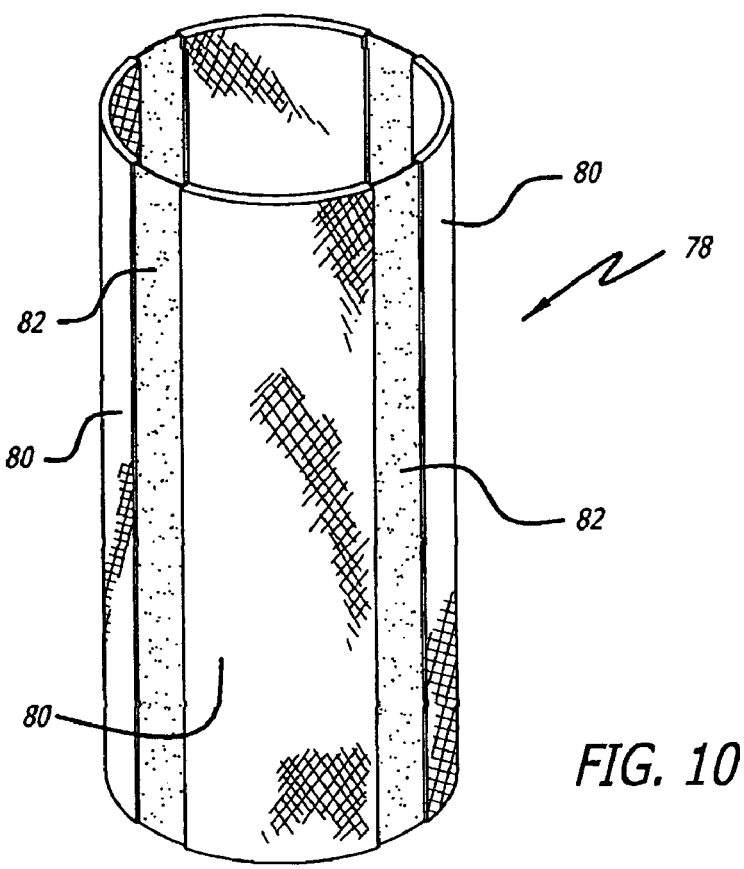
FIG. 10

CAST ASSEMBLY WITH BREATHABLE DOUBLE KNIT TYPE PADDING

FIELD OF THE INVENTION

This invention relates to orthopedic casts or supports.

BACKGROUND OF THE INVENTION

Concerning prior work of others, reference is made to U.S. Pat. No. 5,334,442, granted Aug. 2, 1994, which discloses "triple layer" fabric portions adhered to both sides of a pliant sheet impregnated with water hardenable material. However, this proposed construction appears to be relatively complex, will be costly to produce, and the construction precludes uses where overlapping bonding of the casting material is appropriate. Reference is also made to U.S. Pat. No. 5,807,295, in which the possibility of using double knit material as an undercast padding is mentioned. However, no constructional details or specific information is provided.

Orthopedic casts or supports for immobilization of injuries normally include an absorbant soft padding material next to the skin and stiff or rigid outer casting material. Because casts are normally kept on for several weeks, they may become damp or wet from the cast application, sweat, rain, or from swimming, as examples. When the inner padding is wet for long periods of time, it is harmful and irritating to the patient. In severe cases, maceration of the skin can occur.

INVENTION SUMMARY

Accordingly, a principal object of the invention is to provide a quick drying cast system which will readily permit drying, following sweating or wetting of the cast by rain or swimming, as examples.

In accordance with one illustrative embodiment of the invention, a cast padding is formed of double knit type material with a relative close weave or knit on the side to face the skin, and a relatively open weave or knit on the side away from the skin, for increased air circulation. The double knit type construction provides open areas underneath the hardened casting material for air to circulate, resulting in quicker and more efficient drying of both the cast and cast padding. These open spaces also allow the water to easily flow out of the padding, meaning that the double knit construction does not hold as much water initially as do many of the more traditional padding materials like foam, felt, batting, etc. This ability to allow water to flow out rapidly, in combination with the air circulation after application, results in a finished cast assembly that will have a much quicker drying time than traditional cast applications. In-house drying tests have shown that using spacer material in place of cast padding allows a traditional cast to dry out approximately twice as fast as the commonly used synthetic padding. The spacer cast padding may be supplied in one of three different forms: (1) in a tubular configuration of various sizes, (2) as blanks, or (3) as rolls with various widths. In a tubular configuration the injured part of the body, such as a forearm, may be slid into the tube or sleeve much the same way as stockinette is currently applied, and a hardenable material applied over it. Because the spacer material has its own intrinsic padding properties, there is no need for additional moisture absorbing padding as with traditional casting methods. In roll form, the double knit padding can be continuously rolled around the injured anatomy in an overlapping fashion very similar to the manner in which traditional cotton or synthetic cast padding is currently applied. The material may also be cut into a shaped blank which has been designed for a specific portion of the anatomy, and this blank is placed on the body and trimmed if necessary prior to the application of the hardenable cast material.

The hardenable material may be of any conventional type; but preferably has openings in it to facilitate additional air circulation. The outer hardenable material may be a blank of double knit material and/or a single-layered knit tape, both of which would be impregnated with a known water hardenable material, such as urethane, and both of which would preferably have holes through the material for air circulation, as noted above. It is again noted that conventional casting tape may be employed by itself around the double knit padding; and that a blank, perhaps with a thumb hole, could also be used by itself as the outer casting material.

Instead of water activated hardening material, other hardening materials may be employed, such as a two part system in which hardening occurs soon after mixing the two materials and applying them to the casting fabric.

The double knit type padding preferably extends beyond the casting material around the edges thereof by a short distance such as ¼ inch or ⅛ inch, to avoid scratching or abrasion of the skin by the potentially rough edges of the hardened material. The padding material may be folded back over the edges and adhered to the cast material by lamination to create a finished and more comfortable edge.

When reference is made to double knit type material or "spacer" material in the present specification and claims, reference is made to material which has first and second spaced woven or knit fabric layers, with an openwork matrix of filaments extending between the two fabric layers, and with the filaments being integrally woven or knit into the two layers. To provide sufficient padding for the anatomy the spacer should have a thickness of between 0.100" and 0.25", preferably between 0.125" and 0.15". One preferred configuration for the matrix of filaments is an "X" or crisscrossing pattern of the interconnecting filaments. This will ensure that the fabric has a high resistance to compression and will maintain the distance between the first and second layers which is desirable for increasing the drying characteristics of the fabric. This configuration also ensures that the necessary padding and protection are provided for the anatomy under the hardened casting material.

It is also noted that the assembly of the double knit type padding with the breathable construction and outer casting material, also with holes or comprised of loosely woven or knit material, preferably does not have any further outer covering, so that circulation of air is promoted. If the hardenable material is made of a knit material with many holes, additional strength may need to be added by adding either single or multiple layers of additional casting material in select areas to act as stays and providing additional strength in only the necessary areas.

It is difficult to knit a spacer in a tubular form with the appropriate movement to account for the varying diameters of the anatomy. For example, it is necessary that the padding material have sufficient radial stretch to conform to the varying diameters of the hand, wrist, and forearm without wrinkling. An acceptable extensibility range is 50% to 200% with the ideal extensibility being approximately 100%. It is preferable that the radial extensibility be greater than the lengthwise extensibility. To increase the radial extension of the tubular configuration, it is possible to use spacer material in combination with other materials. It is preferable that this second material is one that has large extensibility. A single strip or multiple strips of the second material can be integrated into the tube, thereby creating multiple longitudinal strips of the spacer material and the second material. These strips would be sewn or bonded together to create a more flexible and conformable tube structure. Another method of increasing the bias movement of the spacer material to better conform to the anatomy is by knitting it into alternating thick and thin strips and then forming it into a tube. The thick portions would be double-knit and the thin portions would be a single-knit with the potential for larger movement. This type of construction can be achieved during a single manufacturing step, greatly reducing the labor associated with creating a tubular spacer over the above mentioned method of sewing in separate strips of material.

Increased conformability can also be achieved by contouring the tubular spacer to more closely replicate the curves of the anatomy. For example, for an upper extremity application, it is possible to vary the diameter of the tube by knitting the appropriate shape and/or sewing it into a specific pattern to allow for the differences between the hand, wrist and forearm.

Modifications to the tubular geometry can be made to provide for easier application. These can include, but are not limited to, creating a pre-made thumbhole or providing a thumb piece for receiving or supporting the thumb.

The padding can also be provided in the form of a blank shaped to fit the specific part of anatomy to be immobilized. The blank can be either knitted into the appropriate shape during manufacturing or cut to the shape after the material is manufactured. In one embodiment, this blank can be provided in an oversized shape and then trimmed to the correct dimensions during application in order to accommodate the most sizes of anatomy as possible with one size blank.

It is also possible, but not necessary, to supply the spacer material with a type of adhesive that will stick to either the skin or underlying stockinette. A similar layer of adhesive can be used on the opposite side of the padding, adjacent to the coated blank, to prevent the water hardenable resin from penetrating the padding while stored in the package. This same layer of adhesive can serve an additional role of attaching a covering material to the padding in the areas of the padding extending beyond the edge of the coated blank around the entire product.

The blank can also be supplied with varying thicknesses to provide more padding in strategic locations, i.e., over bony prominences. This additional padding can be achieved either during the knitting process or added as additional pieces after manufacturing and secured by adhesive or similar means. Additional padding can also be placed in an appropriate location prior to the application of the casting material to give the patient further protection from the cast saw during cast removal. Padding pieces may also be provided and placed over bony prominences, around the edges (i.e. thumbhole) or any other necessary areas to provide further protection for the user.

A third form that the spacer padding material can be provided in is in roll form. It would be applied by wrapping it around the part of the anatomy to be immobilized. Because of the thickness and resiliency of the spacer material, only one layer of wrapping would be necessary to provide sufficient padding. When using traditional padding, two to four layers must be used, resulting in a longer application time, more water retention and decreased air circulation. To decrease the bulk in the overlapping areas, the edges of the roll may by thermoformed or knitted to be lower in profile.

To increase the rapid drying characteristics of the double-knit cast padding, the fibers used to make the material can be made of any material and then coated with a hydrophobic material, such as SCOTCHGARD®. It is also possible to use a combination of different fibers in specific constructions within the spacer matrix and outer layers. Knitting with specific fiber combinations can create a wicking effect to pull the moisture away from the skin. This wicking action will increase the drying properties underneath a cast or support applied over the spacer cast padding.

Another feature of the invention allows for increasing air circulation under the cast by knitting or forming holes throughout the hardenable spacer material blank or any other casting material applied over the padding.

Other objects, features and advantages of the invention will become apparent from a consideration of the following detailed description and from the accompanying drawings.

BRIEF DESCRIPTION OF THE DRAWINGS

FIG. 4 is a perspective view of the assembly, showing the padding and casting material, with the patient's arm not shown;

FIG. 5 is a cross-sectional view taken along line 5-5 of FIG. 4;

FIG. 10 shows a tubular assembly of spacer material padding with strips of high bias movement alternated with the spacer material; and FIG. 11 shows the padding assembly of FIG. 10 mounted on the forearm of a patient.

DETAILED DESCRIPTION OF THE PREFERRED EMBODIMENTS

Figure 1:
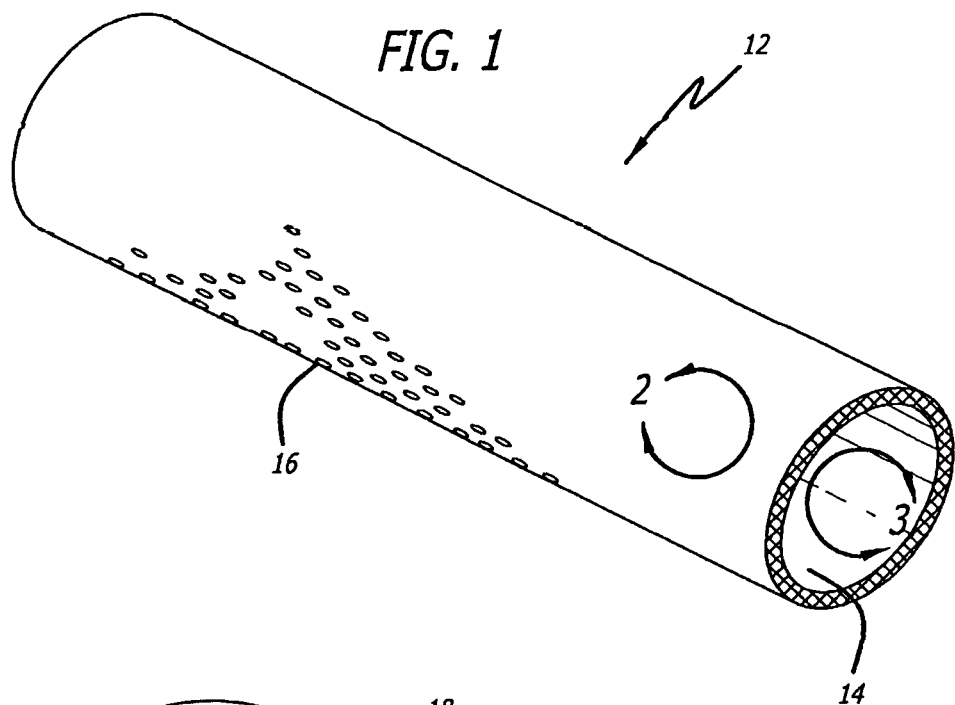
FIG. 1 shows tubular cast padding made of double knit type material in which the inner layer of the double knit material is more finely knit than the outer layer.
Figure 2:
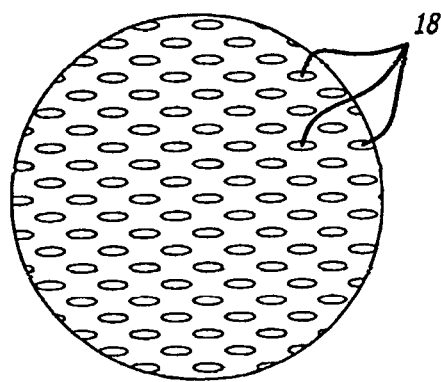
FIG. 2 is an enlarged view of the outer area of the padding shown in FIG. 1.
Figure 3:
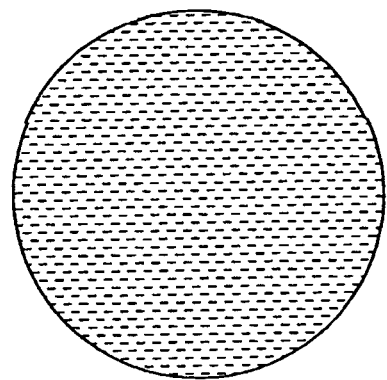
FIG. 3 is an enlarged view of the more finely knit surface on the inside layer of the double knit type padding shown in FIG. 1.

Referring more particularly to the drawings, FIG. 1 shows a tube 12 of double knit type material, which is intended for use as padding underneath a cast or support. As mentioned above, the double knit material involves an inner layer such as that shown in FIG. 3 and at area 14 of FIG. 1 of a finely knit or woven structure to provide a smooth surface next to the skin providing additional comfort for the patient. Incidentally, another method resulting in a smooth comfortable surface on the inner face of the padding material is to laminate a single layer of fabric to one surface of the double knit material. The outer surface of the double knit material, for example at area 16 and as shown enlarged in FIG. 2, is of a relatively coarse woven or knit structure and may have openings such as those shown at 18 in FIG. 2, to permit improved air circulation through the outer portion of the padding 12. In one sample product, the openings 18 are approximately ⅛-inch long and are 1/16-inch in their lesser transverse dimension. The outer surface should have approximately 20% to 65% open area with about 40% open area being preferable.

It is further noted that the inner and outer layers 14 and 16 may be formed of different fibers. More specifically, the inner layer 14, next to the skin, may be knit from hydrophobic fibers, and the outer layer 18 can be knit of hydrophilic fibers, thereby "attracting" the moisture from the skin and drawing it away from the hydrophobic layer 14. An alternative configuration utilizes both hydrophobic and hydrophilic fibers in the same inner layer 14. The hydrophobic fibers would be arranged closest to the skin and the hydrophilic fibers closest to the spacer yarns. This arrangement will draw any moisture away from the skin towards the spacer yarns to be rapidly evaporated. This configuration not only improves the quick dry feature of the padding, but also gives the patient a much dryer surface next to their skin in much less time. Hydrophobic materials which may be used include polyester and polypropylene; while hydrophilic materials would include fibers made up of a bundle of fine fibers, or polyester monofilaments which are etched to retain moisture. Incidentally, monofilament yarns will hold less water and dry out quicker than multifilament yarns. It is preferable that a quick dry padding be composed mainly of monofilament yarns or lower filament yarns for this reason. Incidentally, a "lower" filament yarn is a yarn formed of only one or only a few monofilaments so that it is still substantially hydrophobic.

FIG. 4 shows cast padding 12 and casting material 13 as they might appear in use, but without the inner forearm around which they would be mounted. The padding 12 may have a soft, finely woven or knit inner surface and a loosely woven or knit and/or apertured outer surface as described above in connection with FIGS. 1-3. The water hardenable casting material 13 may or may not be apertured as well, with the apertured configuration increasing air circulation and reducing drying time. Both of these materials 12 and 13 may be provided with a thumbhole 14.

The padding 12 may be knit in a tubular manner, as shown in FIG. 1, or it may be formed as a flat blank of double knit type material and formed into tubular configurations by the stitching 17 as shown in FIG. 4. The edges of the casting material 13 may optionally be overlapped in the area 15, and the overlapping layers laminate together in this area creating circumferential support. Concerning dimensions, the padding tube 12 may, for example, be approximately two inches in diameter, and may be any desired length. It may be provided in various diameters and lengths for snugly fitting over portions of the body such as the forearm or lower leg, for specific examples. Other methods of forming a flat blank into a tube include adhesive, ultrasonics, taping, or any other method of bonding the edges together.

FIG. 5 shows a cross section of the spacer or double knit type configuration of the padding 12 and the casting material 13 of FIG. 4 through the line 5-5. In practice, the padding 12 is initially applied to the injured part of the anatomy, such as the forearm; and subsequently the casting material 13 is dipped in water for activation and is applied over the padding 12. It is also an option to dip both layers into the water at the same time and apply them both as a single unit.

Preferably, the casting material 13 may be initially flat and then may be wrapped around the injured portion of the anatomy; and can be optionally secured in place by overlapping, by VELCRO® type hook and loop fastening, by straps, or by a supplemental casting tape.

Figure 6:
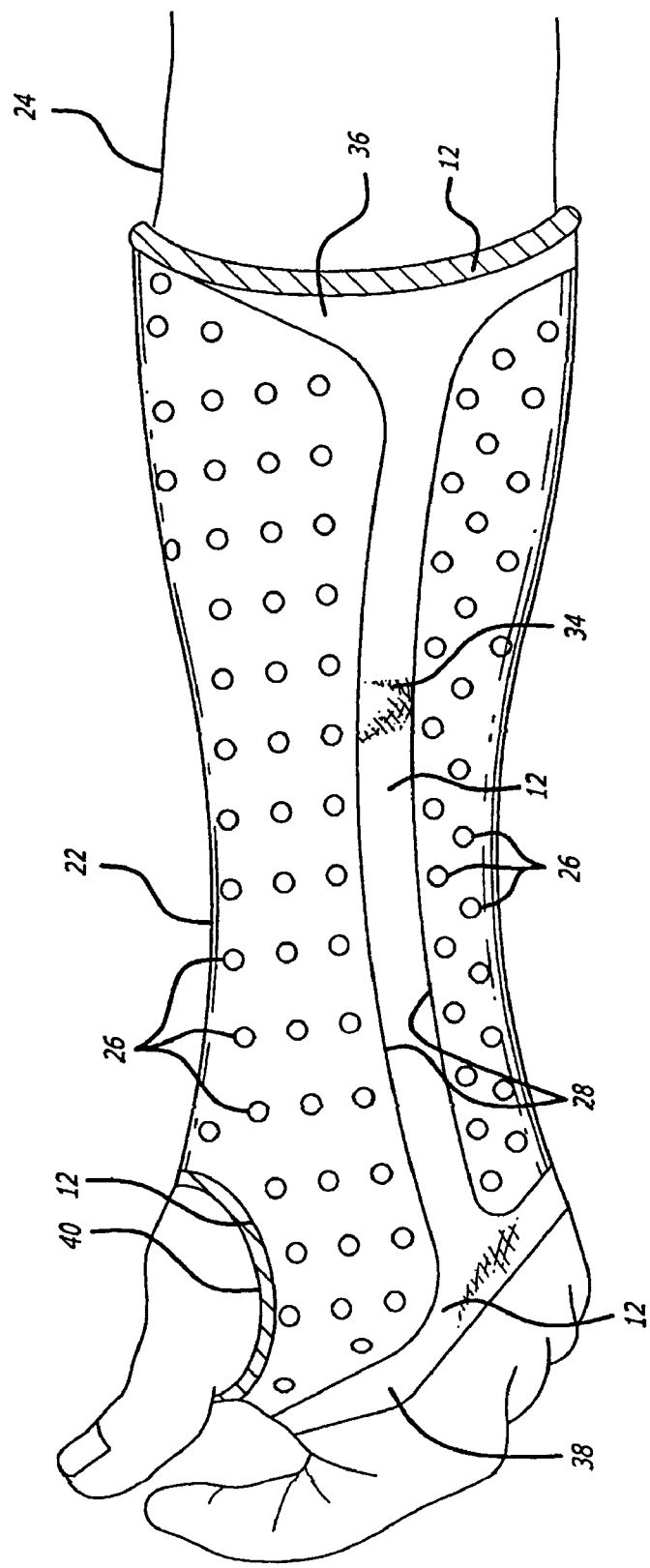
FIG. 6 shows a casting or support assembly as applied to the forearm of a patient.

Now, turning to FIG. 6 of the drawings, the double knit type padding material is shown at reference number 12 extending beyond the edges of the water hardenable type double knit material 22 as indicated at reference 36, 38, and 40. While finishing the cast, this excess padding can then be folded back over the edges of the material 22 to create a finished edge and provide the wearer with more comfort. The water hardenable double knit material 22 is a shaped blank with the thumbhole forming part of the blank, and it is dipped in water prior to being applied to the forearm 24. The water hardenable material 22 becomes rigid to provide immobilization within the usual time period for standard casting products following application, such as 3 to 7 minutes. It is possible to make the water hardenable material 22 with apertures 26, which extend all of the way through both layers of the water hardenable material to increase airflow and facilitate more rapid drying.

The casting material 22 may be held in place in any desired manner. For example, the edges 28 may overlap and bond to one another in these areas by lamination of the layers. Alternatively, a casting tape may be employed to wrap around the forearm and secure the casting material 22 in place. The water hardenable casting tape may also be provided with relatively large holes or apertures to permit air circulation through to the padding 12.

As a further alternative, a single additional strip of either hardenable or non-hardenable casting material may be employed to bridge across the opening 34 between the two edges of the water hardenable blank 22, with the activatable water hardenable material bonding and laminating the layers together.

Where casting tape is employed in addition to the water hardenable blank 22, the openings 26 in the blank 22 may be relatively large to ensure adequate air circulation all the way from the outer surface of the water hardenable material through to the padding material 36. However, even without openings in blank 22, the spacer type padding provides significantly decreased drying time of the assembly because of the previously mentioned air circulation beneath the cast. The spaced apart layers of the double knit construction allow for the evaporation of water to occur not only through the inner and outer surfaces, but also through the two open ends of the finished cast.

Figure 7:
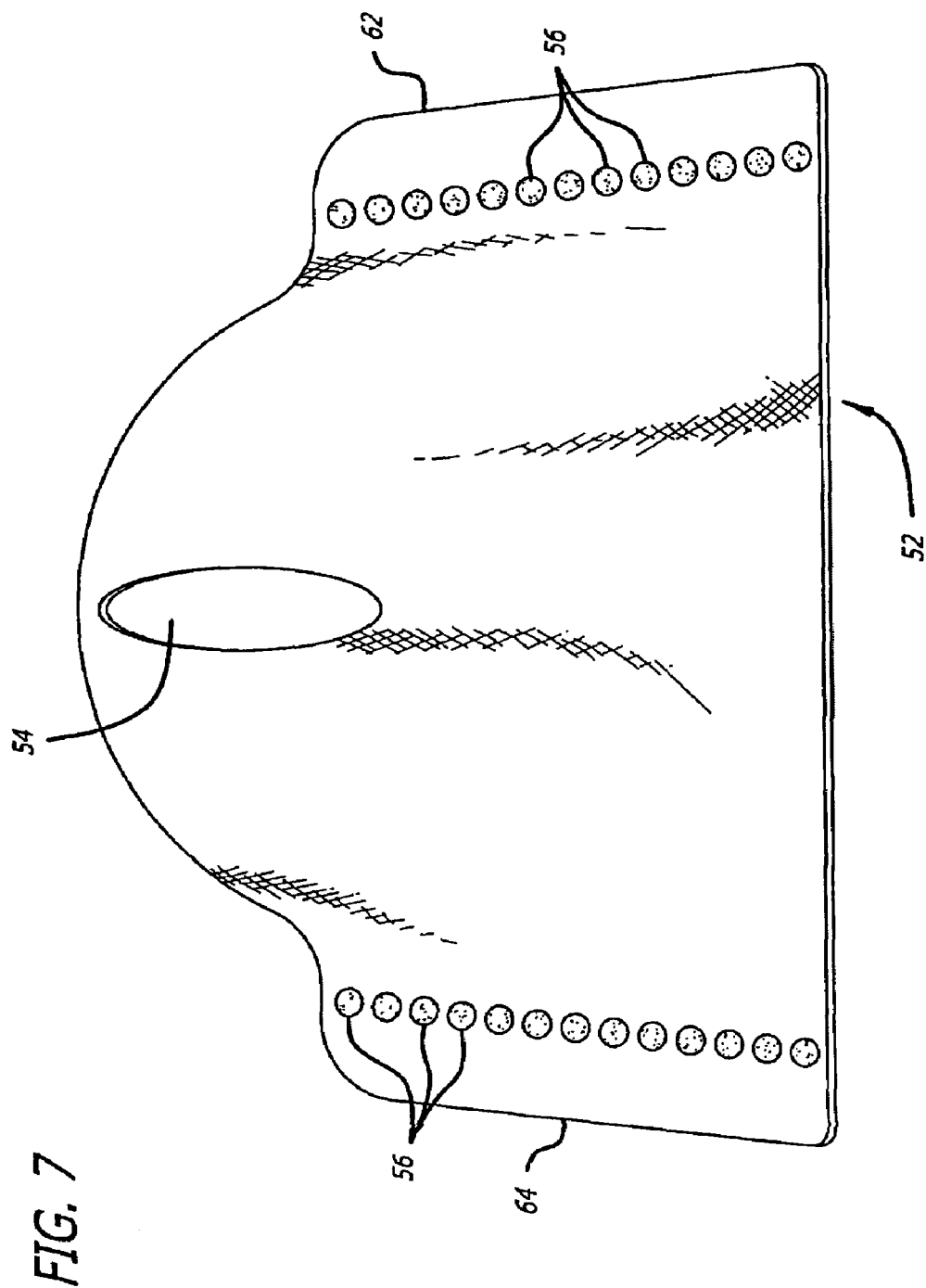
FIG. 7 shows a padding blank formed of spacer or double knit type material.
Figure 8:
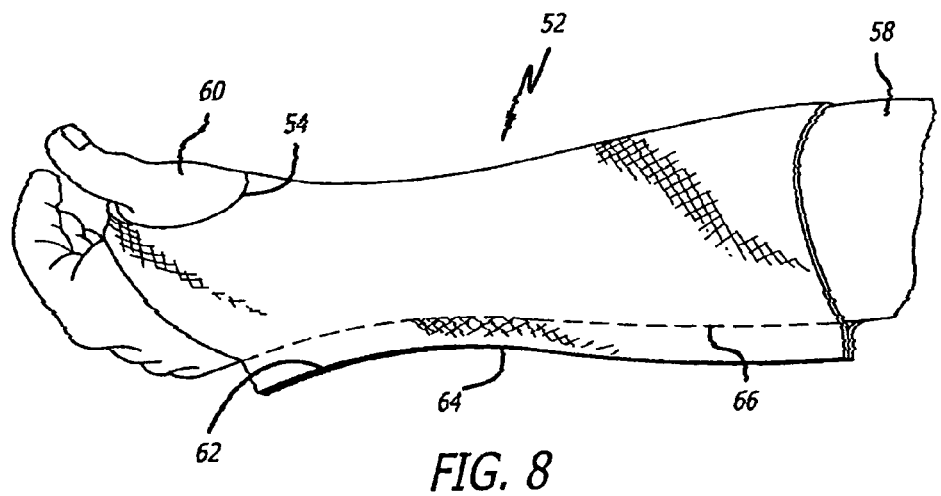
FIG. 8 shows the blank of FIG. 7 applied to the forearm of a patient.

Referring now to FIGS. 7 and 8 of the drawings, FIG. 7 shows a blank 52 of spacer or double knit type padding material for the forearm, with a thumb hole 54. Also shown in FIG. 7 are optional dots of pressure-sensitive adhesive 56 which may be present to help maintain the padding material in place on the anatomy by engaging with either the underlying stockinette or skin of the patient as the casting material is applied over it. Alternatively, if the pressure-sensitive adhesive is applied on the opposite side of the padding blank and extends over the entire surface, it serves the additional function of preventing the resin from the casting material from getting into and through the spacer padding.

In FIG. 8, the blank 52 is shown applied to the forearm 58 of a patient with the thumb 60 extending through the thumb hole 54. The edges 62 and 64 are preferably trimmed, for example as indicated by the dashed line 66 so that the padding blank fits smoothly on the forearm of the patient, preferably without overlapping edges. Additional clips or tape may be used to secure the two free edges together without gaps. In use, the casting or splinting material would then be applied over this padding.

Figure 9:
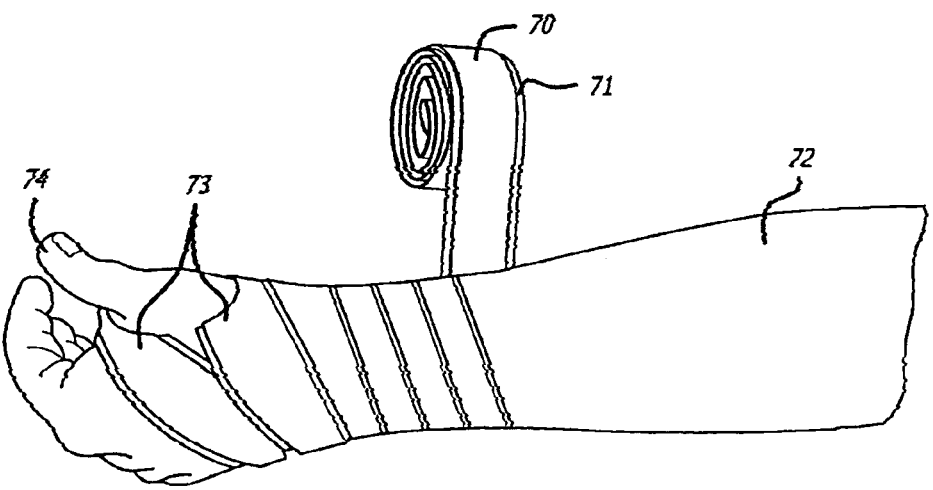
FIG. 9 shows spacer cast padding in the form of a tape being wrapped onto the forearm of a patient.

FIG. 9 shows another embodiment where a roll of spacer material undercast padding 70 is wrapped over the forearm 72 of a patient. The tape 70 may have a notch 73 adjacent the thumb 74 to make it fit more smoothly. Once wrapped, the free end of the tape may be secured in place by pressure sensitive adhesive, clips, etc., if necessary. In order to prevent bulk in the overlapping areas, the longitudinal edges 71 of the spacer padding may be thermoformed or knitted flat.

Referring now to FIGS. 10 and 11, an undercast padding assembly 78 is shown before and after application to a forearm respectively. It includes wide strips of spacer or double knit type material 80 and narrow, more stretchable strips 82 interleaved between the broader strips of spacer material. The strips 82 have large inherent bias movement or stretchable qualities so that the entire assembly will readily follow the shape of the anatomy, such as the forearm 84 as indicated in FIG. 11. The strips may be of LYCRA®, stockinette material or any other woven or knitted material with sufficient bias movement, for examples. It is further noted that the stretchable strips or areas 82 may be single layer knit materials formed integrally with the spacer or double material 80 as the material is knit or woven.

Concerning the double knit type material, it may be made on a double needle bar Raschel warp knitting machine, available from the Mayer Company of Germany. Double knit type fabrics knitted into a shape and/or of varying thickness can be made on machines available from H. Stoll GmbH & Co. of Stollweg 1, D-72760 Reutlinger, Germany. Tubular double knit type material may be made on specialized circular knitting machines.

In the foregoing detailed description, one preferred embodiment of the invention is disclosed. Various modifications and somewhat different constructions may be employed without departing from the spirit and scope of the invention. Thus, for specific example, in some cases, the apertured casting blank need not be of double knit material but casting blanks or tapes of other apertured or very open knit fabrics may be employed, with the apertured double knit padding material underlying the casting material. It is also noted that, in addition to the forearm, the padding material and outer water hardenable material may be employed on casting assemblies for the foot or leg or other portions of the anatomy. It is further noted that instead of discrete holes, the outer layer of the double knit type padding material may be very coarsely woven or knit so that visible openings are present in the fabric; and the inner layer of the double knit padding may be somewhat more tightly woven or knit so that no visible openings are present through this inner layer. Concerning the filaments to be employed, a flat monofilament may be employed, as it has excellent hydrophobic properties. It is also contemplated that the undercast padding spacer material may be treated with anti-microbials, an anti-odor treatment or the like to minimize the odor beneath a cast once it has been worn for an extended period of time. Concerning activation of the casting material, this can be accomplished by dunking the casting material in water, either before or after application to the patient. Accordingly, the present invention is not limited to the precise embodiments shown in the drawings and described in detail hereinabove.

We Claim:

1. A cast or support assembly comprising:
   a compressible padding layer including a padding material formed of double knit type fabric material having an inner layer of finely woven or knit material with openings defining a smooth surface structure, and an outer layer of coarsely woven or knit material with openings therethrough spaced from said inner layer by an open work matrix of filaments which are integrally woven or knit into said inner and said outer layers of woven or knit material, the outer layer openings being larger than the openings of the inner layer, the padding layer being devoid of a hardening material such that the padding layer remains compressible upon exposure to water; and
   a hardenable layer including an outer water hardenable double knit type material overlying said padding material, said outer double knit material being impregnated with water activatable hardening material to provide the desired immobilization;
   wherein the matrix of filaments are formed from wicking yarns to facilitate moisture transfer from the inner layer to the outer layer;
   whereby the spacing between layers of said padding material in addition to the holes therethrough, facilitate air circulation to accomplish rapid drying of the cast assembly.

2. A cast or support assembly as defined in claim 1 wherein said outer water hardenable double knit material is in the form of a blank of irregular configuration formed to fit a portion of the anatomy.

3. A cast or support assembly as defined in claim 1 wherein said outer water hardenable double knit material has holes therebrough.

4. A cast or support assembly as defined in claim 1 wherein said padding material is formed into a tubular configuration.

5. A cast or support assembly as defined in claim 1 wherein said padding material is in the form of a blank of irregular configuration formed to fit a portion of the anatomy.

6. A cast or support assembly as defined in claim 1 wherein said padding material extends beyond the edges of said water hardenable material to avoid scratching the patient by the edges of the hardened cast material.

7. A cast assembly as defined in claim 1 wherein said assembly including the inner padding material and the outer hardenable material is free of additional layers of material to promote air circulation and drying.

8. A cast assembly as defined in claim 1 wherein said water activatable hardening material is a urethane.

9. A cast or support assembly as defined in claim 1 wherein said padding inner layer is predominantly hydrophobic and said padding outer layer is predominantly hydrophilic.

10. A cast or support assembly as defined in claim 1 wherein said outer layer has approximately 20% to 65% open area.

11. A casting or splinting assembly comprising:
    a compressible padding layer including a double knit type padding material consisting an inner layer and an outer layer spaced apart from one another, and filaments extending between and spacing said layers apart, said filaments being integrally woven or knit into both said inner and said outer layers, said outer layer having openings of substantial size for air circulation and greater in size than openings defined along the inner layer, the inner layer having a finely knit or woven structure forming a smooth surface structure, the padding layer being devoid of a hardening material such that the padding layer remains compressible upon exposure to water; and
    a hardenable layer including casting fabric impregnated with water hardenable material overlying the outer layer of said padding material, said casting fabric having substantial openings, for increased air circulation.

12. A cast assembly as defined in claim 11 wherein said padding material is formed into a tubular configuration.

13. A cast assembly as defined in claim 11 wherein said padding material is in the form of a blank of irregular configuration formed to fit a portion of the anatomy.

14. A cast assembly as defined in claim 11 wherein said padding material extends beyond the edges of said water hardenable material to avoid scratching the patient by the edges of the hardened cast material.

15. A cast assembly as defined in claim 11 wherein said assembly including the inner padding material and the outer hardenable material with holes, is free of additional layers of material to promote air circulation and drying.

16. A cast assembly as defined in claim 11 wherein said water activatable hardening material is a urethane.

17. A cast assembly as defined in claim 11 wherein said casting fabric is a double knit type material.

18. A cast assembly as defined in claim 11 wherein said casting fabric is in the from of a blank of irregular configuration formed to fit a portion of the anatomy.

19. A cast or support assembly comprising:
- a compressible double knit padding material including an inner layer of hydrophobic material, and an outer layer of hydrophilic material, and filaments extending between and spacing the inner and outer layers apart, the inner layer being of a finely knit or woven structure defining a smooth surface structure, the filaments being integrally woven or knit into both the inner and the outer layers, the inner and outer layers each having a plurality of openings, the openings of the outer layer being greater than the openings of the inner layer and shaped of substantial size for air circulation, the padding layer being devoid of a hardening material such that the padding layer remains compressible upon exposure to water;
- and outer water hardenable material overlying said padding material, said outer material being impregnated with water activatable hardening material to provide the desired immobilization;
- whereby the inner layer of hydrophobic and outer layer of hydrophilic material included in said padding material facilitate the wicking of moisture away from the skin to accomplish rapid drying of the cast assembly.

20. A cast or support assembly as defined in claim 19 wherein the inner hydrophobic layer is formed at least in part of flat monofilaments.

* * * * *